United States Patent [19]

Falvai et al.

[11] Patent Number: 5,782,807
[45] Date of Patent: Jul. 21, 1998

[54] RELEASABLY LOCKING INTRODUCER DEVICES

[75] Inventors: John Falvai; Frank Bimbo. both of Peterborough; Richard S. Riddle. Keene, all of N.H.

[73] Assignee: TFX Medical Incorporated. Jaffrey, N.H.

[21] Appl. No.: 546,499

[22] Filed: Oct. 20, 1995

[51] Int. Cl.⁶ .................................................. A61M 5/178
[52] U.S. Cl. .................................... 604/164; 604/165
[58] Field of Search .................................. 604/160, 161, 604/164, 165, 264

[56] References Cited

U.S. PATENT DOCUMENTS

| | | | |
|---|---|---|---|
| 4,233,974 | 11/1980 | Desecki | 604/165 |
| 4,596,559 | 6/1986 | Fleischhacker | 604/170 |
| 4,772,266 | 9/1988 | Groshong | 604/164 |
| 4,966,588 | 10/1990 | Rayman | 604/165 |
| 5,064,414 | 11/1991 | Revane | 604/168 |
| 5,160,323 | 11/1992 | Andrew | 604/165 |
| 5,275,583 | 1/1994 | Cranich | 604/264 |
| 5,279,597 | 1/1994 | Dassa | 604/165 |
| 5,290,294 | 3/1994 | Cox | 604/164 |
| 5,391,152 | 2/1995 | Patterson | 604/165 |
| 5,437,645 | 8/1995 | Urban | 604/165 |

Primary Examiner—Robert A. Hafer
Assistant Examiner—Jeffrey D. Carlson
Attorney, Agent, or Firm—David G. Conlin; Peter F. Corless; Dike, Bronstein, Roberts & Cushman, LLP

[57] ABSTRACT

A releasably locking dilator/sheath medical introducer device is provided having a dilator with a non-circular cross-sectional shape to enable insertion of a catheter, guide wire and the like into a patient. More particularly, the invention provides an introducer device that has dilator with a non-circular cross-sectional shape, particularly a substantially oval cross-sectional shape, and that comprises a releasable lock for the dilator and the circumscribing sheath components of the device. In preferred embodiments, the introducer device also includes a visual indicator and/or a tactile indicator to conveniently inform a user of the device whether the dilator/sheath assembly is in a locked or unlocked position. In another aspect, a releasably locking introducer device is provided that has a dilator that can rotate within a circumscribing sheath component wherein the dilator includes a proximal end component that can rotate around the longitudinal axis of the device relative to and independently of the dilator and sheath components to releasably lock the dilator within the circumscribing sheath.

31 Claims, 3 Drawing Sheets

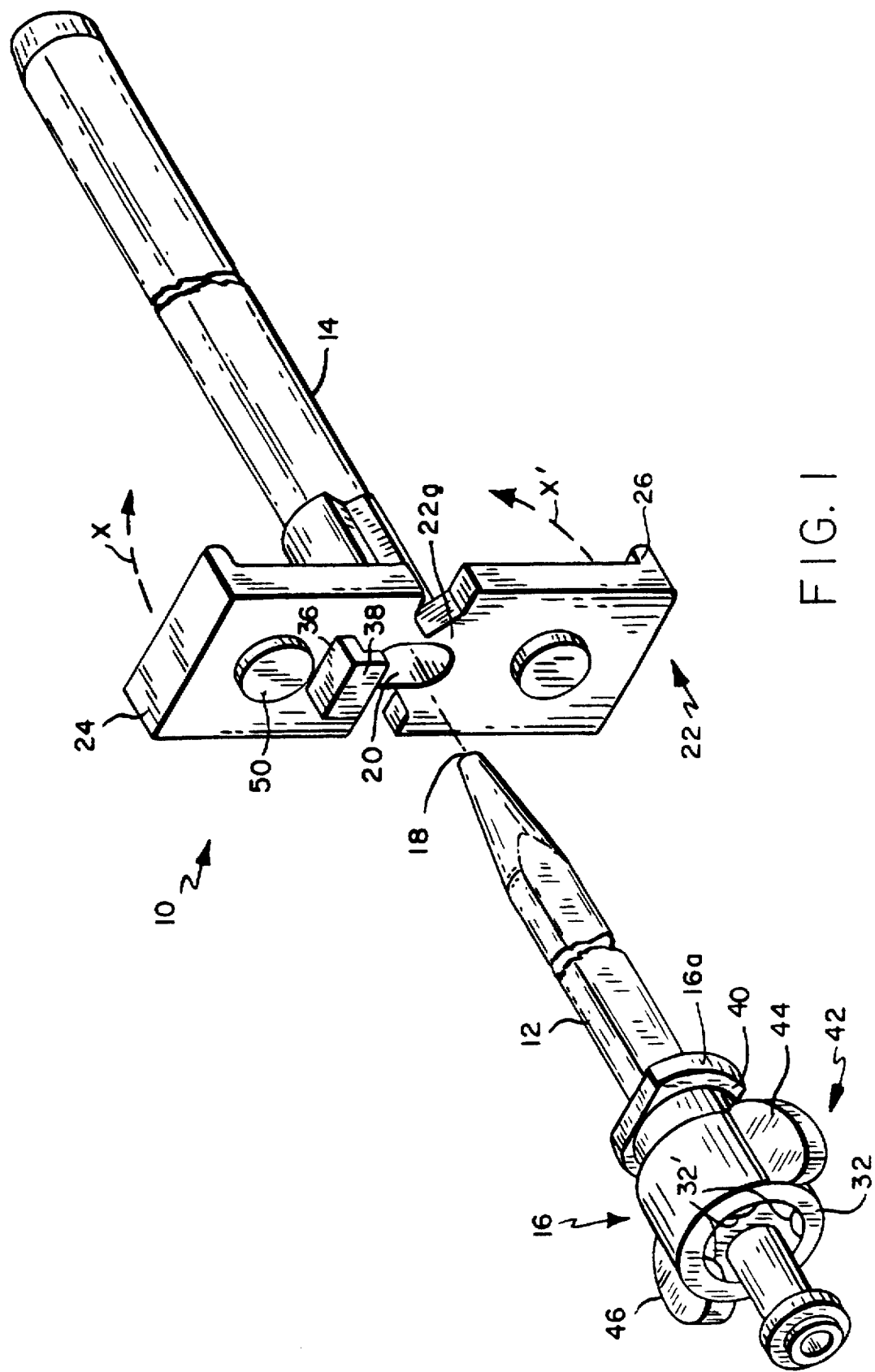
FIG. I

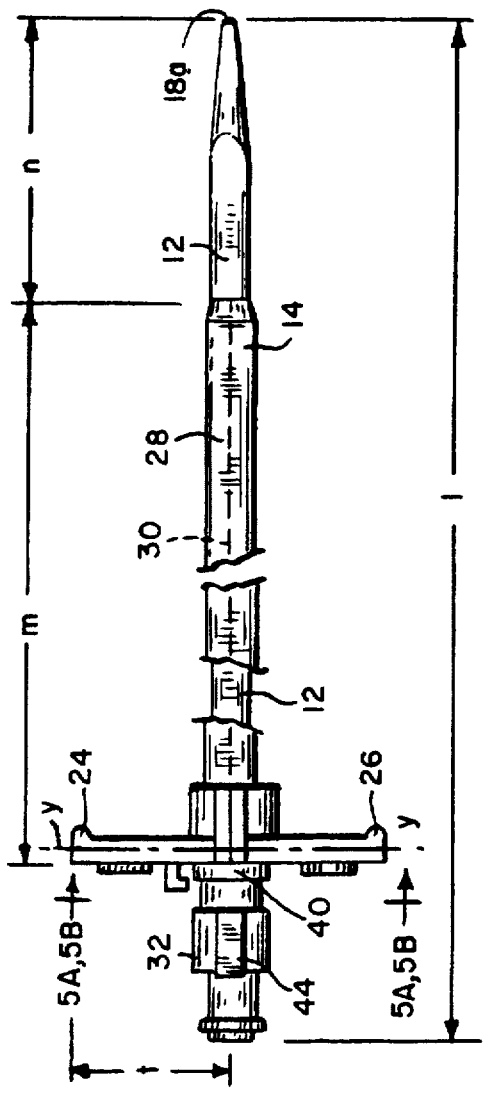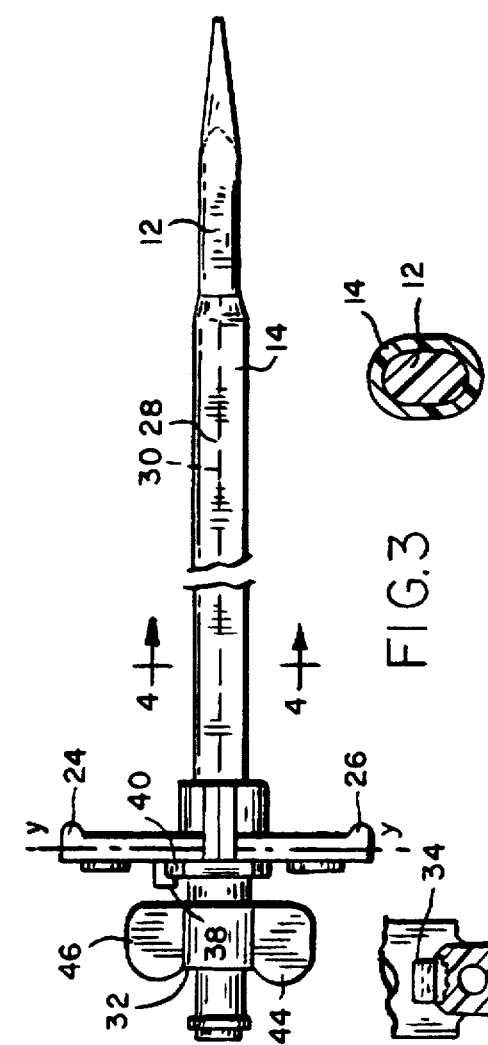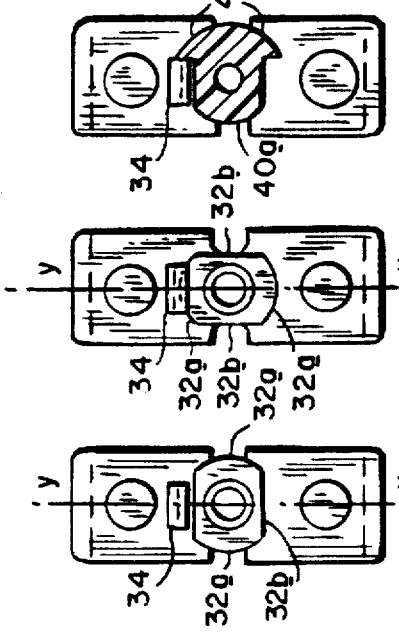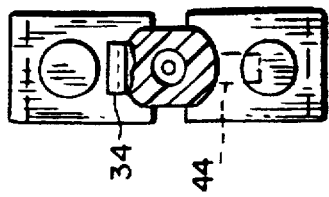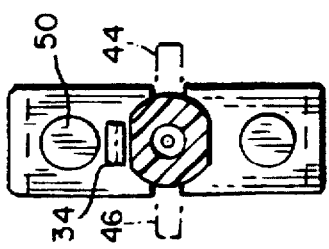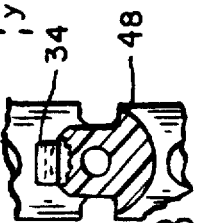

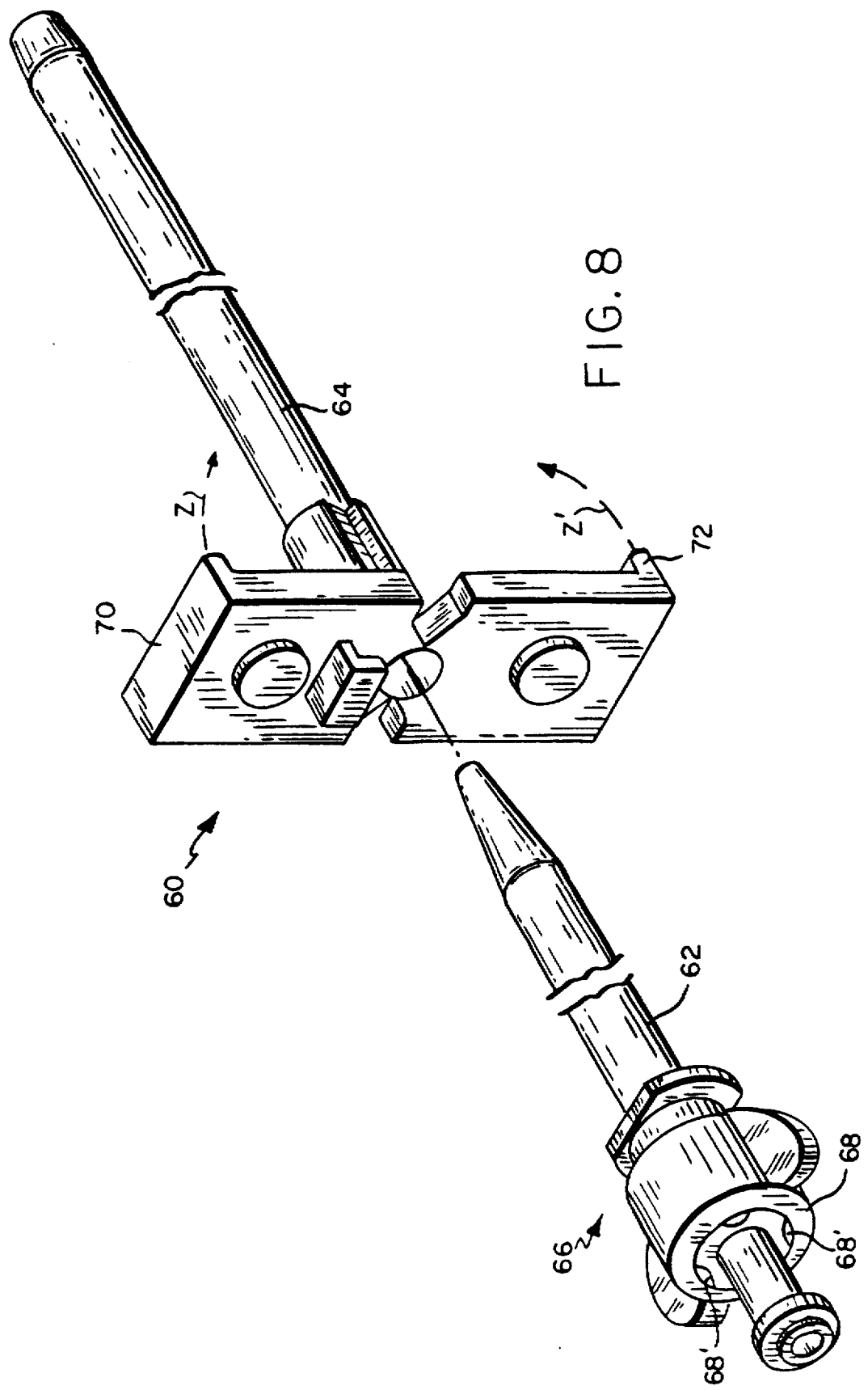

RELEASABLY LOCKING INTRODUCER DEVICES

BACKGROUND OF THE INVENTION

Dilator/sheath introducer devices have been employed for inserting catheters, guide wires and the like into patients. A typical procedure provides for insertion of a dilator or needle encased within a splittable sheath into the vasculature of a patient. After insertion, the dilator may be removed leaving the sheath protruding from the patient's vein. A diagnostic or therapeutic catheter (e.g. a central venous access catheter) or guide wire or other object such as a capsule, is then threaded through the sheath into the patient. The encasing sheath is then typically longitudinally sheared and removed from the catheter or the like and the patient such as by applying opposing force to opposed wings or tabs of the introducer device. See U.S. Pat. Nos. 5,334,157; 5,221,263; 5,141,497; 5,098,392; 4,772,266; and 4,243,050.

It is possible during manipulation and initial insertion of the introducer device for the dilator and sheath components to become separated. Such separation of the dilator/sheath will cause problems during a medical procedure such as when the distal end of the circumscribed dilator is being initially inserted into a patient.

Certain devices have been previously reported that have a dilator with a substantially circular cross-sectional shape and means for releasably locking the dilator to a circumscribing sheath (which also has a substantially circular cross-sectional shape). See U.S. Pat. No. 4,243,050 to Littleford. However, the locking mechanism of such prior devices has required dilator and sheath components having a substantially circular cross-sectional shape because the releasable lock relies on rotation of the dilator within the sheath component. Such requisite rotation is generally not possible where the cross-sectional shape of the dilator and sheath components is other than circular.

Introducer devices that comprise dilator and sheath components having non-circular cross-sectional shapes, particularly substantially oval cross-sectional shapes, are useful for a number of medical procedures. For example, such devices have been used for sub-clavian insertions and other procedures where it is desired to make an insertion narrower than that provided by a dilator having a circular cross-sectional shape.

Additionally, it is possible that in some circumstances when using a circular cross-sectionally shaped dilator, it may be undesirable to axially rotate the dilator and/or sheath components in order to lock or unlock those components. For example, such rotation may potentially interfere with a guide wire or other object that is threaded through the dilator/sheath assembly.

It thus would be desirable to have a dilator/sheath introducer device comprising a dilator component having a non-circular crosssectional shape and that includes a releasable lock to avoid undesired movement of the dilator/sheath assembly. It also would be desirable to have releasably locking dilator/sheath introducer devices, including devices that have dilator and sheath components that have substantially circular cross-sectional shapes, that do not require axial rotation of the dilator and sheath components in order to releasably lock those components.

SUMMARY OF THE INVENTION

In a first aspect, the invention comprises a dilator/sheath introducer device that contains a dilator with a non-circular crosssectional shape and a releasable lock to avoid undesired movement of the dilator with respect to the sheath. The device is highly useful to insert a catheter, guide wire and the like into a patient, especially where a relatively narrow insertion is desired.

In a preferred device of the invention, the dilator comprises a proximal end hub component that can rotate relative to and independent of the dilator and sheath to thereby releasably lock the dilator and sheath. The dilator hub component can be of a variety of configurations to provide the releasable lock. Preferably the releasable lock comprises mating surfaces on the rotatable dilator hub component and the sheath proximal end. Mating of those surfaces releasably locks the dilator/sheath assembly to prevent undesired axial movement of the dilator. Rotation of the dilator hub component separates those surfaces to unlock the dilator/ assembly and permit withdrawal of the dilator from the sheath as desired.

Preferably the introducer device of the invention also includes a visual indicator to provide clear visual indication to a device user that the dilator/sheath assembly is in a locked or unlocked position. Such a visual indicator affords significant advantages relative to prior devices such as the device of the above mentioned U.S. Pat. No. 4,243,050. (That prior device can entail relatively careful visual inspection to determine if the sheath and dilator components are in a locked or unlocked position. Such a careful inspection may be quite inconvenient, particularly during the course of a medical procedure.)

The visual indicator is suitably one or more protrusions on the dilator proximal end, preferably on opposing sides of the dilator. Particularly preferred are outwardly extending flanges. The visual indicator also may be configured to aid handling and manipulation of the introducer device.

The introducer device of the invention also may comprise a tactile indicator to conveniently inform a user of the device whether the dilator/sheath assembly is in a locked or unlocked position. The tactile indicator preferably comprises a positive stop or inhibitor which provides the device user tactile indication of whether the assembly of the dilator with circumscribing sheath is releasably secured (locked) so that axial movement of the dilator within the circumscribing sheath is avoided, or whether the dilator/sheath assembly is disengaged (unlocked) so that the dilator may be removed from the sheath, e.g. after the sheath has been inserted into a patient's vein or artery. In a preferred embodiment, the positive stop comprises a plurality of mating surfaces on the proximal ends of the dilator and sheath wherein the surfaces mate to indicate to a device user that the dilator/sheath assembly is locked or unlocked. Such mating surfaces are suitably of a variety of configurations so long as the desired tactile indication is provided. Preferably the surfaces mate to inhibit or prevent further rotation of the dilator hub component to thereby indicate the assembly is in a locked or unlocked position.

In a second aspect of the invention, a releasably locking introducer device is provided that has dilator and circumscribing sheath components wherein the dilator can axially rotate within the circumscribing sheath. In this aspect of the invention, the dilator and sheath components are typically substantially circular in cross-sectional shape. The dilator includes a proximal end hub component as described above that can rotate around the longitudinal axis of the device relative to and independently of the dilator and sheath components to releasably lock the dilator within the circumscribing sheath. This releasable lock avoids any need of rotation of the dilator and/or sheath components during locking or locking of the dilator/sheath assembly.

The invention also includes methods for inserting a catheter, guide wire or the like into a patient comprising inserting an introducer device of the invention into a patient and inserting a catheter, guide wire or the like through the device into the patient.

Other aspects of the invention are disclosed infra.

BRIEF DESCRIPTION OF DRAWINGS

FIG. 1 shows an above view of an introducer device of the invention having separated sheath and dilator components each with a non-circular cross-sectional shape;

FIG. 2 shows a partial cut-away side view of an introducer device of the invention where the dilator is circumscribed by the sheath component;

FIG. 3 shows an above view of an introducer device of the invention where the dilator is circumscribed by the sheath component;

FIG. 4 is a cross-sectional view taken along the line 4—4 of FIG. 3;

FIGS. 5A and 5B show top views in cross-section along line 5A,5B of FIG. 2 wherein the dilator/sheath assembly are in an unlocked position (FIG. 5A) and a locked position (FIG. 5B);

FIGS. 6A and 6B show top views of a further preferred introducer device of the invention with the dilator circumscribed by the sheath, and the dilator/sheath assembly are in an unlocked position (FIG. 6A) and a locked position (FIG. 6B);

FIGS. 7A and 7B show top cross-sectional views of a further preferred introducer device of the invention that includes a tactile indicator; and FIG. 8 shows a further preferred introducer device of the invention wherein the dilator can rotate within the circumscribing sheath component.

DETAILED DESCRIPTION OF THE INVENTION

The sheath component of an introducer device of the invention has a bore adapted to receive a dilator for insertion into a vein of a patient while circumscribed by the sheath. The dilator component is adapted to be inserted within the sheath and preferably is also bored. Typically, the sheath component is splittable, i.e. the sheath may be axially sheared such as along diametrically opposed longitudinal score lines as desired. Additionally, the sheath component preferably will comprise a hub portion at the sheath proximal end to facilitate such shearing. (in accordance with conventional practice, "proximal end" designates herein the specified end closest to the medical personnel manipulating the introducer device, and "distal end" designates herein the specified end closest to the patient.) Preferably, the sheath hub contains a pair of opposing wings or tabs that can facilitate axial shearing of the sheath.

Referring now to the Drawings, where particularly preferred introducer devices of the invention are depicted, FIGS. 1–3 show introducer device 10 that includes dilator 12 and sheath 14. Dilator 12 has dilator hub 16 at the dilator proximal end and typically contains bore 18 through its length.

Dilator 12 has a non-circular shape for at least a portion of its length. In some preferred embodiments, the distal end of such a dilator may be more circular, especially at tip 18a of the dilator distal end. Preferably, other than the dilator hub portion and the dilator distal end, dilator 12 suitably has a non-circular shape for essentially all its length as generally shown in FIG. 1. Dilator 12 preferably is substantially oval-shaped in cross-section as shown in FIGS. 1 and 4, although the dilator also could have other non-circular cross-sectional configurations where rotation of the dilator within the circumscribing sheath is inhibited or prevented.

Sheath 14 includes bore 20 to snugly receive dilator 12. Sheath 14 contains sheath hub 22 which preferably includes opposed wing or tab portions 24 and 26 to aid axial shearing of the sheath, specifically by directing pressure to wings 24 and 26 along directions x and x' as shown in FIG. 1. Preferably sheath 14 also includes axially extending, diametrically opposed score lines 28 and 30 as shown in FIGS. 2 and 3 to facilitate axial shearing upon engaging wings 24 and 26. Dilator component 12 is inserted into and is circumscribed by sheath 14 during use of device 10 as clearly depicted in FIGS. 2 and 3. Axial rotation of dilator 12 within circumscribing sheath 14 is prevented or at least inhibited as a result of the preferred design of the sheath. That is, sheath 14 preferably has a cross-sectional shape that substantially matches that of dilator 12 in order to snugly circumscribe the dilator and thereby provide a comparatively narrow profile.

Dilator hub 16 includes rotatable component 32 that preferably comprises at least a portion of the dilator/sheath releasable lock. Dilator 12 and sheath 14 can be releasably locked when dilator 12 is fully inserted into sheath 14 as shown in FIGS. 2 and 3, i.e. where dilator hub bottom face 16a mates with sheath hub top face 22a. As used herein, the terms "locked", "secured" and the like with regard to the dilator/sheath assembly indicate that axial withdrawal of the dilator out of the sheath is substantially prevented during regular use of the device. In preferred aspects of the invention, dilator hub 16 has a substantially circular cross-sectional shape around which the rotatable component 32 can axially rotate.

A variety of locking mechanisms can be employed for purposes of the present invention. A preferred assembly is shown in the Drawings where non-threaded mating surfaces integral to the dilator and sheath or the hub portions thereof provide the releasable lock. More specifically, lock flange 34 comprising upstanding portion 36 with laterally extending flange 38 on sheath hub 22 is adapted to engage lip 40 on dilator hub 16, specifically on rotatable component 32. With dilator 12 inserted fully into sheath 14 (i.e. where dilator hub bottom face 16a mates with sheath hub top face 22a), component 32 can be independently rotated with respect to the dilator/sheath longitudinal axis so that lip 40 is positioned under flange 38, thereby releasably locking the dilator/sheath assembly and preventing undesired axial movement of dilator 12 out of sheath 14. It should be appreciated that while component 32 can be rotated around such a longitudinal axis independently of the dilator/sheath assembly, dilator 12 and sheath 14 are precluded from such rotation as a consequence of the non-circular cross-sectional shape of those components.

Rotatable component 32 positioned on the proximal end of dilator 12 may be of a variety of configurations provided the component can provide the desired releasable lock of the dilator and sheath components. A preferred system provides that rotatable component 32 is press or snap fitted onto mounting flanges 32' that protrude from the dilator hub as can be seen in FIG. 1. Mounting flanges 32' together provide a substantially circular surface on which component 32 can be mounted and axially rotated. The diameter of the dilator hub with mounting flanges 32' should be sufficient so that component 32 fits snugly over flanges 32' while still permitting easy rotation of component 32 by a device user. If desired, component 32 may have one or more inwardly extending lips that rest on the top and/or bottom ends of flanges 32' to further ensure that component 32 will remain fixed on mounting flanges 32' as desired.

Other locking mechanisms also may be employed such as other non-threaded integral mating flange configurations. For example, the sheath proximal end may comprise a rotatable component that is axially rotated to mate with a surface on the dilator proximal end to thereby releasably lock the dilator/sheath assembly. However, it is generally preferred that such a rotatable component is present on the dilator.

A threaded or luer lock system also could be employed where the dilator and sheath are releasably locked through such a threaded or luer lock engagement, e.g. where the dilator hub distal end screws into the proximal end of the sheath hub, although such a threaded or luer lock system may be less convenient during use of the device. A separate non-integral locking piece (or at least non-integral to at least one of the sheath and dilator components) such as a clip to releasably attach the sheath and dilator components, although such a non-integral locking device is generally less preferred because of the bulk of the non-integral component and if it entails an additional item that must be accounted for during a medical procedure.

Device 10 also may include a visual indicator 42 to provide convenient visual indication to a device user that the dilator/sheath assembly is in a locked or unlocked position. A variety of indicators may be employed such as colored markers on the device, particularly on the dilator hub, or some type of protrusion on the dilator hub or other selected configuration on the dilator proximal end. One or more protrusions on the dilator proximal end is a generally preferred visual indicator.

In a preferred embodiment clearly depicted in FIGS. 1 and 3, visual indicator 42 suitably comprises opposing, outwardly extending protrusions or tabs 44 and 46 positioned on the dilator proximal end. During use of the device, alignment of tabs 44 and 46 indicate whether the dilator/sheath assembly is in a locked or unlocked position. Thus, for device 10 shown in the Drawings, alignment of tabs 44 and 46 along axis y (FIG. 3) of sheath wing portions 24 and 26 visually indicates the dilator/sheath assembly is in a locked position, and substantially perpendicular alignment of tabs 44 and 46 with respect to axis y (see FIG. 2) visually indicates the dilator/sheath assembly is in the unlocked position. Also, if desired, manufacturer or vendor identification or other information may be displayed on tabs 44 and 46 or rotatable component 32.

Another suitable visual indicator with protrusions on the dilator proximal end is shown in FIGS. 6A and 6B. As shown in those figures, two opposing faces 32a of the rotatable component 32 protrude with respect to two other opposing faces 32b that are aligned perpendicularly with respect to the protruding faces 32a. More particularly, faces 32a protrude and are rounded while the nonprotruding faces 32b are substantially flat. Alignment of protruding faces 32a along axis y visually indicates the dilator/sheath assembly is in a locked position, and substantially perpendicular alignment of faces 32a with respect to axis y visually indicates the dilator/sheath assembly is in the unlocked position.

It is also preferred that such visual indicators are configured to aid a user's handling and manipulation of the introducer device. For example, outwardly extending tab protrusions may have indentations along the length thereof to form finger grips to facilitate handling of the device by medical personnel. The substantially flat surfaces 32b as shown in FIGS. 6A and 6B and discussed above also will aid manipulation of the device.

Device 10 also may include a tactile indicator to inform a device user whether the dilator/sheath assembly is in a locked or unlocked position without the need for any visual inspection of the device. A variety of configurations can be employed so long as the device user is provided tactile indication of whether the dilator/sheath assembly is releasably locked so that axial movement of the dilator within the circumscribing sheath is avoided, or whether the dilator/sheath assembly is unlocked so that the dilator may be removed from the sheath.

A preferred indicator is a positive stop that comprises a plurality of mating surfaces on the proximal ends of the dilator and sheath wherein the surfaces mate to indicate to a device user that dilator/sheath assembly is locked or unlocked. Preferably at least one surface on the sheath mates with at least one surface on the dilator to provide tactile indication of locking or unlocking.

In one particularly preferred embodiment depicted in FIGS. 7A and 7B of the Drawings (which figures are in cross-section along a line such as 5A,5B of FIG. 2), indicator flange 48 extends laterally outward from each side of dilator lip 40 and mates (upon axial rotation of rotatable component 32) with lock flange 34 (particularly portion 36 thereof) to provide tactile indication that the dilator and sheath are in an unlocked position as shown in FIG. 7A. The dilator and sheath components then can be placed in a locked position by rotation of component 32 in the opposite direction. FIG. 7B shows the dilator/sheath assembly in a locked position, with lip 40 secured under flange 38, and wherein component 32 has been rotated about 90° C. from the unlocked position depicted in FIG. 7A. Other tactile indicators also may be suitably employed. For example, dilator lip 40 may contain a lateral flange extending perpendicular to flange 48 shown in FIGS. 7A–7B that would abut locking flange 34 to provide tactile indication that the dilator/sheath assembly was in a locked relationship. Such an additional indicator flange could be used in combination with flange 48 as shown so that tactile indication would be provided both upon locking and unlocking of the dilator/sheath assembly. Such an additional indicator flange may suitably extend from lip face 40a shown in FIG. 7A. Additionally, rather than abutting a locking flange, an indicator flange on the dilator hub may mate with a separate surface on the sheath not associated with the releasable dilator/sheath lock. However, it is generally preferred that the tactile indicator is configured in combination with, i.e. is an integral part of, the releasable dilator/sheath lock to enhance ease of manufacture.

Still further, the tactile indicator could be incorporated into rotatable component 32. For example, further rotation of component 32 could be inhibited or prevented after unlocking of the dilator/sheath assembly by movement of component 32 to the position shown in FIG. 5A. Such a tactile indictor could be provided by a groove that circumscribes a portion of the inner surface 32s of component 32 to limit rotation of component 32 around flanges 32' between the two positions shown in FIGS. 5A and 5B.

Device 10 also may include a lead-in section (not shown) at the sheath proximal end adapted to facilitate insertion of a dilator, guide wire, catheter or the like. The lead-in section is preferably downwardly tapered toward the sheath distal end, such as being conically or funnel shaped. Also, such a lead-in section may be suitably notched in alignment with score lines 28 and 30 to facilitate axial shearing of sheath 14.

Device 10 also may be supplied to a medical facility in a variety of sizes, including different lengths as well as different cross-sectional widths of the sheath and dilator components as may be required for varying medical procedures. The respective sizes may be marked on the introducer devices in a variety of ways, including e.g. color-coded or numerical markers positioned on the sheath hub or similar marker 50 on the dilator hub.

Sheath component 14 is preferably formed in an insert molding process as is known in the art wherein the sheath 14 is extruded and then the sheath hub 18 with wings 24 and 26 are molded directly thereon. It also would be possible to separately form the sheath hub and then adhere the hub onto the separately formed sheath such as by a suitable adhesive. Although generally less preferred, it is also possible to interpose a mounting unit such as a plastic strip between the sheath hub and the sheath. The components of device 10 can be formed from a number of materials as will be appreciated by those skilled in the art. For example, the sheath and sheath hub are suitably each from a polyethylene. Sheath 14 is preferably formed from a fluorinated ethylene-propylene resin (FEP), and also could be formed from other fluorinated resins, e.g. a tetrafluoroethylene polymer such as TEFLON. Dilator 12 and dilator hub 16 are preferably also made by such a insert molding process where the dilator is extruded and the dilator hub molded directly thereon. The dilator and dilator hub are suitably formed from a polyethylene. The dilator is preferably formed from a fluorinated ethylene-propylene resin (FEP), and also could be formed from other fluorinated resins, e.g. a tetrafluoroethylene polymer such as TEFLON. In addition to polyethylene, both the sheath hub and dilator hub also may be suitably formed from a polypropylene, or be of the same composition as the sheath and dilator, respectively, e.g. FEP. For at least some applications, dilator 12 also may be formed from stainless steel or other metal with sharpened distal end. Rotatable component 32 can be suitably formed of a wide variety of materials, and preferably is the same material as the dilator hub, e.g. a polyethylene, polypropylene, FEP, a tetrafluoroethylene polymer or the like. Component 32 can be produced by a wide variety of procedures, including e.g. an insert or injection molding process.

Suitable dimensions of the components of an introducer device of the invention having components with non-circular cross-sectional shape can suitably vary rather widely and can be readily determined by those skilled in the art based on the present disclosure. In general, dilator 12 and sheath 14 should have dimensions to permit insertion within a selected vein of a patient, and sheath 14 should have a dimensions sufficient to accommodate a catheter, guide wire or the like. For some preferred applications, the cross-sectional dimensions of non-circular shaped sheath 14 is suitably about 0.276 to 0.281 inches by about 0.201 to 0.206 inches and may suitably be tapered from such dimensions its distal end as depicted in FIGS. 2 and 3. The cross-sectional dimensions of non-circular shaped dilator 12 is suitably about 0.242 to 0.247 inches by about 0.167 to 0.172 inches and preferably is tapered from such dimensions at its distal end as shown in FIGS. 1–3 to facilitate insertion of the dilator into a patient. Preferably the overall length of introducer device 10, represented as length I in FIG. 2, is between about 8.375 and 8.750 inches, with the length of sheath 14 (distance m in FIG. 2) being between about 6.25 and 6.75 inches, and the dilator extending from sheath distal end (length n in FIG. 2) between about 1.25 and 1.75 inches. Wings 24 and 26 preferably extend from sheath centerpoint to the tab end (distance t in FIG. 2) between about 0.68 and 0.72 inches. Again, these dimensions are for devices for generally preferred applications, and devices of a variety of other dimensions also will be suitable for many applications.

A particularly preferred introducer device of the invention is of the configuration shown in the Drawings, wherein the overall length of introducer device 10 (length I) is 8.50 inches; the length of sheath 14 (length m) is 6.50 inches; dilator 12 extends from sheath distal end (length n) 1.25 inches; the length of dilator 12 with hub thereon is 8.50 inches; and wings 24 and 26 extend from sheath centerpoint (distance t in FIG. 2) 1.40 inches.

As discussed above, in another aspect of the invention, a releasably locking introducer device is provided that has a dilator and circumscribing sheath components wherein the dilator can axially rotate within the circumscribing sheath. In this aspect of the invention, the dilator and sheath components are typically substantially circular in cross-sectional shape. As used herein, the term "circular cross-sectional shape," "substantially circular cross-sectional shape" or the like indicates that a dilator having such cross-sectional shape can axially rotate within a circumscribing sheath also having the same cross-sectional shape during normal use of the introducer device. Also, as used herein, the term "non-circular cross-sectional shape," "substantially non-circular cross-sectional shape" or the like indicates that a dilator having such cross-sectional shape is precluded during normal use from axial rotation within a circumscribing sheath having the same cross-sectional shape during normal use of the device.

The rotatable dilator includes a proximal end hub component as described above (component 32 above) that can rotate around the longitudinal axis of the device relative to and independently of the dilator and sheath components to releasably lock the dilator within the circumscribing sheath. This releasable lock avoids any need of rotation of the dilator and/or sheath components.

FIG. 8 depicts an exemplary introducer device of the invention having a dilator with a substantially circular cross-sectional shape. As shown in that Drawing, the device of this aspect of the invention is substantially the same as the device having a non-circular cross-sectional shape discussed above, but the dilator and sheath components each have a substantially circular cross-sectional shape for each of the lengths thereof. Thus, device 60 includes dilator 62 with circumscribing sheath 64. Dilator hub 66 includes rotatable component 68 that functions the same as rotatable component 32 described above. Device 60 may be suitably formed in the same manner and of the materials and sizes as disclosed above in regard to introducer devices of the invention having a dilator with a noncircular cross-sectional shape.

Rotatable component 68 positioned on the proximal end of dilator 12 may be of a variety of configurations provided the component can provide the desired releasable lock of the dilator and sheath components. As with component 32 discussed above, a preferred system provides that rotatable component 68 is press or snap fitted onto mounting flanges 68' that protrude from the dilator hub as can be seen in FIG. 8. Mounting flanges 68' together provide a substantially circular surface on which component 68 can be mounted and axially rotated. The diameter of the dilator hub with mounting flanges 68' should be sufficient so that component 68 fits snugly over flanges 68' while still permitting easy rotation of component 68 by a device user. Again, as with component 32, if desired component 68 may have one or more inwardly extending lips that rest on the top and/or bottom ends of flanges 68' to further ensure that component 68 will remain fixed on mounting flanges 68' as desired. Other locking mechanisms also may be employed such as other non-threaded integral mating flange configurations. For example, the sheath proximal end may comprise a rotatable component that is axially rotated to mate with a surface on the dilator proximal end to thereby releasably lock<the dilator/ sheath assembly. However, it is generally preferred that such a rotatable component is present on the dilator. A threaded or luer lock system also could be employed where the dilator and sheath are releasably locked through such a threaded or luer lock engagement, e.g. where the dilator hub distal end screws into the proximal end of the sheath hub, although such a threaded or luer lock system may be less convenient during use of the device. Device 60 also may include a tactile indicator, visual indicator and/or a lead-in section in the same manner as disclosed above with respect to visual indicator 42, the tactile indicator (including flange 48) and lead-in section.

An introducer device of the invention may be suitably used as follows for placement of a catheter, guide wire, capsule, etc. in a patient.

The introducer device 10 is inserted into a patient via dilator 12 wherein lip 40 is positioned under flange 38 (see FIG. 5B) to releasably lock the dilator/sheath assembly and prevent the dilator extending upwardly out of sheath 14.

After sheath 14 has been positioned as desired in the patient, the dilator can be removed from the sheath. The dilator/sheath assembly can be unlocked by rotation of component 32 so that lip 40 is not positioned under flange 38 such as shown in FIG. 5A. If the device contains a visual indicator, medical personnel can conveniently determine that the dilator/sheath assembly is in a locked or unlocked position such as by the positioning of tabs 44 and 46 as discussed above.

If the introducer device contains a tactile indicator, the device user also can conveniently determine if the dilator/sheath assembly is in an unlocked or locked position. For example, as discussed above, component 32 can be rotated until tactile indication of unlocking is provided in accordance with the invention, e.g. as shown in FIGS. 7A and 7B where further rotation of component 32 is inhibited by tactile indicator flange 48 abutting portion 36 of lock flange 34. As with a visual indicator of the invention, such tactile indication of unlocking is a significant advantage, particularly during use of the device in a medical procedure, where careful visual examination of the device may be highly inconvenient.

Dilator 12 then may be withdrawn from the sheath 14 with sheath 14 remaining in the vasculature of the patient. A catheter, guide wire or the like then can be threaded through sheath 14 (as may be assisted by a lead-in section in the sheath proximal end as discussed above) and into the vasculature. After desired placement of the catheter, guide wire, etc., sheath 14 is suitably removed by applying force in the directions x and x' of sheath wings 24 and 26 to axially split or shear the sheath such as along score lines 28 and 30.

Introducer device 60 of the invention would be used in the same or similar manner as described above for device 10. Thus, for example, dilator 62/sheath 64 assembly is unlocked by rotation of component 68 around the longitudinal axis of the device so dilator 62 can be axially withdrawn from the sheath. After desired placement of the catheter, guide wire, etc. through sheath 64 and into a patient, sheath 64 is suitably removed by applying downward force in the directions z and z' of sheath wings 70 and 72 to axially split or shear the sheath such as along diametrically opposed score lines along the length of the sheath.

The foregoing description of the invention is merely illustrative thereof, and it is understood that variations and modifications can be made without departing from the spirit or scope of the invention as set forth in the following claims.

What is claimed is:

1. A medical introducer device suitable for inserting a catheter or guide wire into a patient comprising:

a releasably locking dilator and sheath, the sheath having a bore adapted to receive the dilator and the sheath adapted to circumscribe the dilator, the dilator having a non-circular shape for at least a portion of its length which inhibits rotation of the dilator within the circumscribing sheath, a component that completely circumscribes the dilator, the component releasably locking and unlocking the dilator and sheath components and can be operationally secured on the dilator with the dilator separated from the sheath.

2. The device of claim 1 wherein the component is press fitted or snap fitted onto the dilator proximal end.

3. The device of claim 1 wherein the dilator has a non-circular shape for essentially its entire length.

4. The device of claim 3 wherein the dilator has a circular cross-sectional shape at a hub portion of the dilator and the dilator distal end.

5. The device of claim 3 wherein the dilator is oval-shaped in cross-section.

6. The device of claim 1 wherein the component rotates with respect to the dilator to provide a releasable lock of the dilator and sheath.

7. The device of claim 6 wherein at least one surface of the component mates with at least one surface on the sheath to provide a releasable lock of the dilator and sheath.

8. The device of claim 1 wherein the component provides a releasable lock by a threaded mechanism.

9. The device of claim 1 wherein the component provides a releasable lock by a luer lock mechanism.

10. A medical introducer device suitable for inserting a catheter or guidewire into a patient comprising:

(a) a releasably locking dilator and sheath, the sheath having a bore adapted to receive the dilator and the sheath adapted to circumscribe the dilator, the dilator having a cross-sectional shape that enables axial rotation of the dilator within the circumscribing sheath; and (b) a component that can be operationally secured on the dilator with the dilator separated from the sheath, the component being capable of rotating independently of the dilator to releasably lock and unlock the dilator and sheath when the sheath circumscribes the dilator and without relative axial rotation of the dilator and sheath, and the component completely circumscribing the dilator.

11. The device of claim 10 wherein the component is press fitted or snap fitted onto the dilator proximal end.

12. The device of claim 10 wherein the dilator has a circular cross-sectional shape.

13. The device of claim 10 wherein the component rotates with respect to the dilator to provide a releasable lock of the dilator and sheath.

14. The device of claim 13 wherein at least one surface of the component mates with at least one surface on the sheath to provide a releasable lock of the dilator and sheath.

15. The device of claim 10 wherein the component provides a releasable lock by a threaded mechanism.

16. The device of claim 10 wherein the component provides a releasable lock by a luer lock mechanism.

17. A medical introducer device suitable for inserting a catheter or guide wire into a patient comprising:

a releasably locking dilator and sheath, the sheath having a bore adapted to receive the dilator and the sheath adapted to circumscribe the dilator, the dilator having a non-circular shape for essentially the entire dilator length and which inhibits rotation of the dilator within the circumscribing sheath.

18. The device of claim 17 wherein the dilator is oval-shaped in cros-ssection.

19. The device of claim 17 wherein the dilator has a circular cross-sectional shape at a hub portion of the dilator and the dilator distal end.

20. The device of claim 17 wherein the device comprises a component that releasably locks and unlocks the dilator and sheath components.

21. The device of claim 17 wherein the device comprises a component that completely circumscribes the dilator proximal end and releasably locks and unlocks the dilator and sheath components.

22. The device of claim 17 wherein the device comprises a component that press fitted or snap fitted onto the dilator proximal end and releasably locks and unlocks the dilator and sheath components.

23. The device of claim 17 wherein the device comprises a component that rotates with respect to the dilator to provide a releasable lock of the dilator and sheath.

24. The device of claim 17 wherein the dilator and sheath releasably lock by a threaded mechanism.

25. The device of claim 17 wherein the component provides a releasable lock by a luer lock mechanism.

26. A method for inserting a catheter or guide wire into a patient comprising:

(a) providing an introducer device comprising a releasably locking dilator and sheath, the sheath having a bore adapted to receive the dilator, the sheath circumscribing the dilator, a component that completely circumscribes the dilator, the component releasably locking and unlocking the dilator and sheath components and can be operationally secured on the dilator with the dilator separated from the sheath;

(b) inserting the distal end of the device into a patient while the dilator and sheath are releasably locked;

(c) rotating the rotatable dilator component with respect to the dilator longitudinal axis to unlock the dilator and sheath; and (d) withdrawing the dilator from the sheath and inserting a catheter or guide wire through the sheath into the patient.

27. The method of claim 26 wherein the dilator has a non-circular shape for essentially the entire dilator length.

28. The method of claim 26 wherein the dilator has a circular shape for essentially the entire dilator length.

29. The method of claim 26 wherein the sheath is axially split after step (d).

30. A method for introducing a catheter or guide wire into a patient comprising:

(a) providing an introducer device comprising a releasably locking dilator and sheath, the sheath circumscribing the dilator, the dilator having a non-circular shape for essentially the entire dilator length and which inhibits rotation of the dilator within the circumscribing sheath;

(b) inserting the distal end of the device into a patient while the dilator and sheath are releasably locked; and (c) withdrawing the dilator from the sheath and inserting a catheter or guide wire through the sheath into the patient.

31. The method of claim 30 wherein the sheath is axially split after step (d).

* * * * *